United States Patent [19]

Bucsky et al.

[11] 4,287,757
[45] Sep. 8, 1981

[54] INSTRUMENTAL MEASURING METHOD FOR DETERMINING THE SIZE-DISTRIBUTION OF GRAINED MATERIAL

[75] Inventors: György Bucsky, Balatonalmádi; Zoltán Kiss, Veszprém; Lajos Tátrai, Veszprém, all of Hungary

[73] Assignee: Magyar Tudomanyos Akademia Muszaki Kemiai Kutato Intezet, Veszprém, Hungary

[21] Appl. No.: 120,060

[22] Filed: Feb. 11, 1980

[51] Int. Cl.³ ............................................. G01N 15/04
[52] U.S. Cl. ................................... 73/61.4; 73/432 PS
[58] Field of Search ................ 73/61.4, 61 R, 432 PS, 73/438, 32 R, 299

[56] References Cited

U.S. PATENT DOCUMENTS

| 2,436,083 | 2/1948 | Williams et al. | 73/61.4 |
| 2,451,604 | 10/1948 | Barnes | 73/299 X |
| 2,668,365 | 2/1954 | Hogin | 73/32 R X |
| 3,788,146 | 1/1974 | Hartman | 73/61.4 X |
| 3,896,660 | 7/1975 | Valentyik | 73/61.4 |

FOREIGN PATENT DOCUMENTS 2739691 3/1978 Fed. Rep. of Germany ....... 73/61.4

Primary Examiner—Gerald Goldberg
Assistant Examiner—Joseph W. Roskos

[57] ABSTRACT

An instrumental measuring method for determining the size-distribution of grained material is described in which the material is evenly distributed in a fluid then the fluid is let in rest state when the materials gets sedimenting, and during sedimentation the hydrostatic pressure is continuously measured in at least two height regions of the fluid preferably by appropriate pressure sensitive transistors and the difference of the measured hydrostatic pressures is characteristic of the size-distribution of the grained material on the basis of the well-known Stokes' relation.

3 Claims, 2 Drawing Figures

4,287,757

INSTRUMENTAL MEASURING METHOD FOR DETERMINING THE SIZE-DISTRIBUTION OF GRAINED MATERIAL

FIELD OF THE INVENTION

The present invention relates to an instrumental measuring method for the determination of particle-size-distribution of grained materials by means of sedimentation in fluids. This instrumental measuring method is based on and improves the conventional technique of measuring differential pressure being proportional to the difference of specific weights, and which is one of several grain size determining sedimentational techniques utilizing Stoke's relation.

BACKGROUND OF THE INVENTION

Sedimentational methods are generally used for the determination of size-distribution of particles in disperse systems, particularly in suspensions. These methods utilise the Stoke's relation, the essence of which expresses that the velocity of down-streaming particles depends on their sizes. There are several techniques known in the field of sedimentational methods.

In the so-called pipette technique small samples are taken from the suspension by means of pipettes, and the solid material contents of these samples are measured. The greatest drawback of this technique lies in that the continuous sampling process diturbs the sedimenting medium.

According to aerometrical technique sinking bodies of known densities are dipped in the suspension that sink during sedimentation always deeper and deeper. Respective sinking bodies represent respective points of the particle distribution curve. The most dominant drawback of this technique lies in that the sinking bodies can not well be seen and observed in the suspension.

The photosedimentational technique is connected with a series of criteria that can not well be satisfied in the practice, because all particles should be perfectly nontransparent, there should not be light reflection between respective particles, and between particles and the wall of the test tube, and finally the suspension is sufficiently diluted not to allow that two particles can fall in the linear path of light.

In the technique of sedimentational scales, or as it is also called the gravitational cumulative method, it is a general problem that the disc of the scale is completely dipped in the suspension and it may cause a streaming therein, furthermore under the scale disc, owing to the change in density of the suspension, convectional streamings can arise that disturb the measurement.

The general disadvantages of activation analytic methods are well known, they can be carried out only in specially equipped laboratories.

The method according to the invention is directly based on the so-called pressure drop technique, in which the concentration change occuring in the sedimenting suspension is measured as a hydrodynamical pressure difference being proportional to the change in specific weight. There are two alternatives of this known technique.

The first alternative is based on the physical phenomenon according to which in communicating vessels (in the present case in an U shaped tube) the height of two fluid columns with different specific weights, measured from the boundary surface of the two fluids, varies inversely with the specific weight of the fluids.

In the second alternative the pressure difference is measured by means of differential manometer within the sedimentational tube.

The principal drawback of both alternatives of this technique lies in that the change either in the level difference or in the pressure that can be read out from the manometer is very little, whereby the visual reading of the values is difficult and inaccurate. The sedimentational and granulometrical curves should be plotted manually from the measured data. The practical performance of the measurements is difficult which has practically prevented this technique from being widely accepted.

SUMMARY OF THE INVENTION

The object of the invention is to provide an improved method and an apparatus by which the size-distribution of grained material can be measured more accurately and in a less complicated way then heretofore without the drawbacks of conventional methods.

In the invention the measuring principle of the second one of said alternative techniques has been utilized by using a substantially improved apparatus and measuring technique.

According to the present invention an instrumental measuring method is provided for determining the size-distribution of grained material in which the material to be measured is inserted in a fluid so that the particles of the material are substantially evenly distributed in the fluid, e.g. by mixing, thereafter the material is allowed to be sedimented in the fluid, and together with the sedimentation of the material the difference of hydrostatic pressure between at least two height regions in the fluid is continuously measured.

The apparatus for carrying out the above method comprises a pair of pressure sensitive transistors for sensing the hydrostatic pressure in said two height regions, and a signal processing means for providing an output signal from the difference of the outputs of the two pressure sensitive transistors.

The instrumental measuring method enables the continuous measurement and registration of the differential pressure in the form of an analogue electrical signal. The apparatus for carrying out the method comprises pressure sensitive transistors as sensing probes and it provides an output signal that, after recording, shows the sedimentation curve characteristic to the disperse system, or when thin suspension layer is examined shows directly the approximative granulometrical curve.

BRIEF DESCRIPTION OF THE DRAWINGS

The invention will now be described by way of Example in connection with a preferable embodiment, in which reference will be made to the accompanying drawings, in which.

DESCRIPTION OF THE PREFERRED METHOD AND EMBODIMENT

Figure 1:
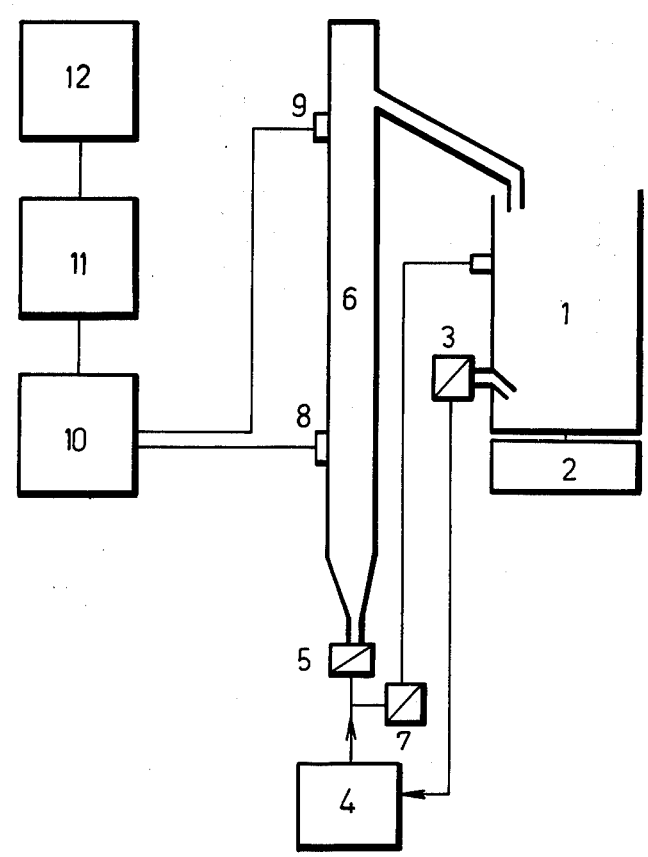
FIG. 1 shows the schematic arrangement of an apparatus for carrying out the method according to the invention.

Reference will be made now to FIG. 1 showing the general arrangement of the apparatus according to the invention. When sedimentation is carried out in a resting fluid, the suspension to be sedimented or the sedimenting fluid and the grained material of appropriate quantity should be place in container 1, in which the stored suspension is kept in a quasi-homogenous condition by means of mixer 2. The suspension is supplied through valve 3 to pump 4, and it is pumped through magnetic valve 5 into sedimenting tube 6. After filling the sedimenting tube 6 the excess suspension falls back to the container 1 through an overflow outlet. When the pump 4 is steadily working, a completely mixed suspension is present in the sedimenting tube 6. In the starting instance of the measurement the magnetic valve 5 breaks and magnetic valve 7 opens the fluid path, the circulating fluid returns then through this latter to the container 1, whereafter the pump 4 stops working. In the moment of operating the valve 5 the suspension in the sedimenting tube 6 will get in rest state and the sedimentation process commences. In two given height regions of the sedimenting tube 6 pressure sensitive transistors 8 and 9 supplied from stabilised power supply 10 and arranged in a difference circuit will measure the hydrostatic pressure changing as the sedimenting process goes on. The measured signal is coupled through measuring amplifier 11 to a line-plotter recorder 12.

The distance of the pressure sensitive transistors 8 and 9 measured from the liquid surface can be adjusted along the longitudinal axis of the sedimenting tube 6, and the mutual distance of the transistors 8 and 9 can also be adjusted together with the height adjustment or separately. By means of appropriate positioning of the transistors the examination can be carried out within predetermined limits in any height of the sedimenting tube 6 with any layer thickness.

When the examination is directed to a suspension column with sufficiently low height or to a thin suspension layer, in the known Stoke's relation for calculating the equivalent diameter, the time factor $\sqrt{t}$ will be equal within a certain error range with t (in the region of $t=1$), in which t expresses the sedimentation time. This is true, because in case of thin layers the sedimentational height and the corresponding sedimentation time (t) is sufficiently small to verify the above approximation. In that case the apparatus records directly the granulometrical curve or an appropriate section thereof.

Figure 2:
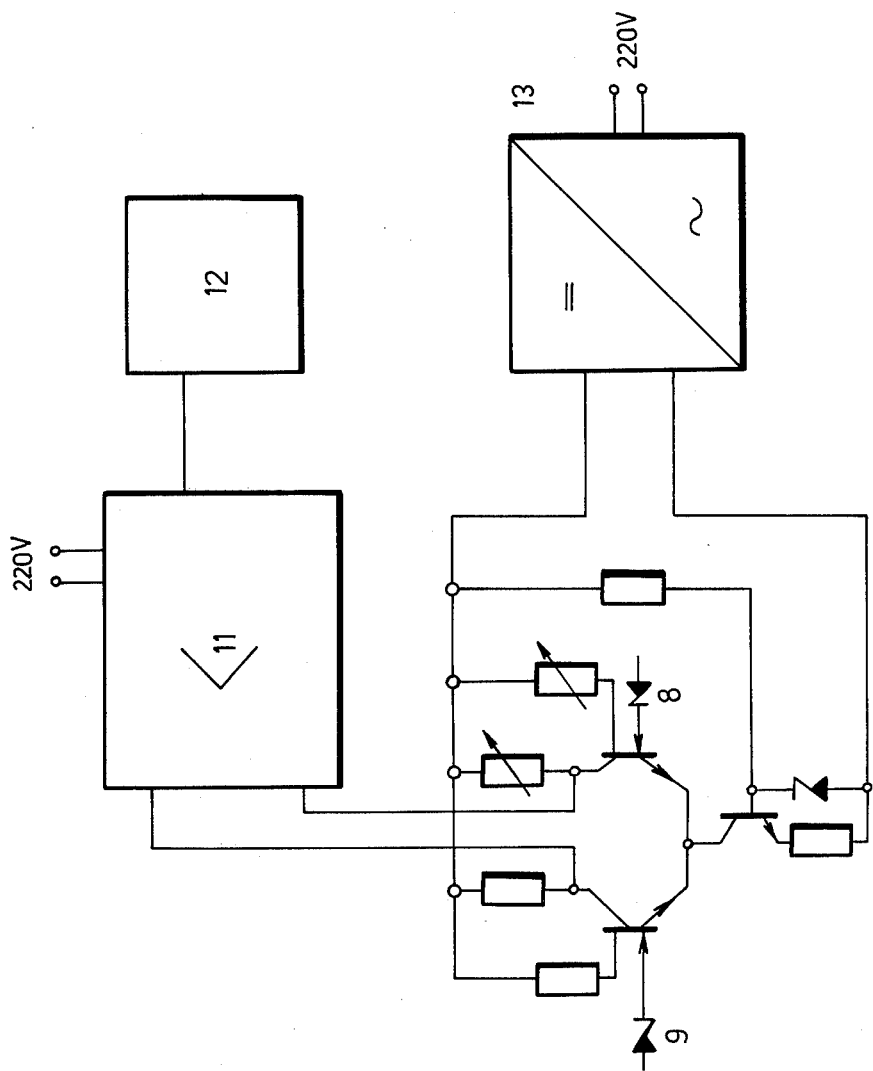
FIG. 2 shows the electrical circuit diagram of the difference circuit formed by a pair of pressure sensitive transistors and the block diagram of the electrical units coupled to the difference circuit.

FIG. 2 shows the electrical circuit diagram of the difference circuit comprising the pressure sensitive transistors 8 and 9. It can be seen from the circuit diagram that the transistors 8 and 9 are connected in a well known difference circuit with common bias. The potentiometers in the collector and base circuits of the transistor 8 serve balancing purposes. Before each measurements when homogeneous suspension is stored in the tube 6 the potentiometers are adjusted so that the output coupled to the input of the amplifier 11 be null. Mains unit 13 supplies the circuits with stabilized dc voltage. The stabilized power supply 10 of FIG. 1 is not indicated separately in FIG. 2.

The circuit shown in FIG. 2 is capable of sensing very small pressure changes.

The advantages of the present invention can be summarized as follows:

During measurements on thin suspension layers it provides directly the approximate granulometrical distribution curve or a section thereof, and in that case it renders a differentiating operation superfluous for evaluation.

It eliminates the greatest error of the original method i.e. the inaccurate reading of small pressure changes.

It can also be used in case of suspensions being transparent and comprising light reflecting particles, and of suspension having comparatively high solid concentration.

The apparatus has not a single element that would disturb the sedimentation process in any way.

We wish to be understood that we do not desire to be limited to the exact details of construction and of the method shown and described, for obvious modifications will occur to a person skilled in the art.

What we claim is:

1. An instrumental measuring method for determining the size distribution of grained material, comprising the steps of inserting the material to be measured into a fluid so that the particles of said material be substantially evenly distributed in said fluid, sedimenting the material in said fluid and continuously measuring the difference of hydrostatic pressure between at least two height regions in said fluid during sedimentation, by developing an electrical signal at each point of measurement in response to the hydrostatic pressure at that point without disturbing the sedimentation by physical sampling.

2. An apparatus for determining the size distribution of a grained material in a fluid wherein the particles of said material are substantially evenly distributed in the fluid and allowed to be sedimented for the measurement, comprising a sedimenting tube, a pair of pressure sensitive transistors arranged on said sedimenting tube for sensing the hydrostatic pressure at two different height regions in said fluid to sense the pressure changes during sedimentation of said grained material in said fluid, and signal processing means responsive to the output of said transistors to provide an output signal proportional to the difference of said transistor outputs representing the difference of the two pressure values prevaling at said two regions.

3. The apparatus as claimed in claim 2, in which both of said pressure sensitive transistors being coupled to respective position adjusting means, whereby their vertical distance and height can be adjusted.

* * * * *